United States Patent
Rioux et al.

(10) Patent No.: US 7,962,197 B2
(45) Date of Patent: *Jun. 14, 2011

(54) RADIATION ABLATION TRACKING SYSTEM AND METHOD

(75) Inventors: Robert F. Rioux, Ashland, MA (US); Paul DiCarlo, Middleboro, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/818,086

(22) Filed: Jun. 17, 2010

(65) Prior Publication Data

US 2010/0256625 A1    Oct. 7, 2010

Related U.S. Application Data

(63) Continuation of application No. 11/298,807, filed on Dec. 9, 2005, now Pat. No. 7,751,869.

(51) Int. Cl.
    *A61B 5/05* (2006.01)
(52) U.S. Cl. .................. 600/427; 600/439; 600/411
(58) Field of Classification Search .................. 600/473, 600/476, 478
    See application file for complete search history.

(56) References Cited

U.S. PATENT DOCUMENTS

| | | |
|---|---|---|
| 6,379,353 B1 | 4/2002 | Nichols |
| 6,454,766 B1 * | 9/2002 | Swanson et al. .............. 606/41 |
| 6,888,919 B2 | 5/2005 | Graf |
| 2002/0077627 A1 | 6/2002 | Johnson et al. |
| 2002/0193685 A1 * | 12/2002 | Mate et al. .................. 600/424 |
| 2004/0024300 A1 | 2/2004 | Graf |
| 2004/0096033 A1 | 5/2004 | Seppi et al. |
| 2004/0158239 A1 | 8/2004 | Behl et al. |
| 2005/0261570 A1 | 11/2005 | Mate et al. |

FOREIGN PATENT DOCUMENTS

| | | |
|---|---|---|
| WO | WO 99/03397 A1 | 1/1999 |
| WO | WO 02/22019 A1 | 3/2002 |
| WO | WO 2005/036124 A2 | 4/2005 |

OTHER PUBLICATIONS

Manning, M.R., et al., "Clinical Hyperthermia: Results of a Phase I Trial Employing Hyperthermia Alone or in Combination with External Beam or Interstitial Radiotherapy," American Cancer Society, vol. 49, 1982, pp. 205-216, XP-002426409.

(Continued)

*Primary Examiner* — Tse Chen
*Assistant Examiner* — Joel F Brutus
(74) *Attorney, Agent, or Firm* — Vista IP Law Group LLP

(57) ABSTRACT

A system and method for treating a target tissue region (e.g., malignant tissue) is provided. A hyperthermic probe is placed into contact with the target tissue region, and the target tissue region is exposed to a therapeutic x-ray radiation beam. The probe is operated to increase the temperature of the target tissue region, thereby facilitating a therapeutic effect of the radiation beam. Image data of the probe containing a fiducial datum is acquired while in contact with the target tissue region, a position of the target tissue region within a treatment coordinate system is determined based on the fiducial datum, and the radiation beam is spatially adjusted relative to the target tissue region based on the determined position of the target tissue region.

20 Claims, 7 Drawing Sheets

OTHER PUBLICATIONS

Vasanthan, A., et al., "Regional Hyperthermia Combined with Radiotherapy for Uterine Cervical Cancers: A multi-institutional Prospective Randomized Trial of the International Atomic Energy Agency," Int. J. Radiation Oncol. Biol. Phys., vol. 61, No. 1, Jan. 2005, pp. 145-153, XP004740506.

Goro, Y., et al., "Advanced Chemoresistant Breast Cancer Responding to Multidisciplinary Treatment with Hyperthermia, Radiotherapy, and Intraarterial Infusion," Int. J. Clin Oncol (2005), Vo. 10, No. 2, Apr. 1, 2005, pp. 139-143, XP019374761.

PCT International Search Report for PCT/US2006/060314, Applicant: Boston Scientific Scimed, Inc., Form PCT/ISA/210 and 220, dated Apr. 19, 2007 (6 pages).

PCT Written Opinion of the International Search Authority for PCT/US2006/060314, Applicant: Boston Scientific Scimed, Inc., Form PCT/ISA/237, dated Apr. 19, 2007 (5 pages).

International Preliminary Report on Patentability (Chapter I of the Patent Cooperation Treaty) from the International Bureau for the related International Application No. PCT/US2006/060314 dated Jun. 19, 2008 (7 pages).

* cited by examiner

RADIATION ABLATION TRACKING SYSTEM AND METHOD

This application is a continuation of U.S. application Ser. No. 11/298,807 filed on Dec. 9, 2005, now issued as U.S. Pat. No. 7,751,869. The above-noted Application is incorporated by reference as if set forth fully herein. Priority is claimed pursuant to 35 U.S.C. §120.

FIELD OF THE INVENTION

The invention relates generally to systems and methods for treating abnormal tissue, such as cancerous tissue, and in particular, the treatment of such abnormal tissue using radiotherapy and hyperthermic therapy.

BACKGROUND

It is known to treat abnormal tissue, such as cancerous tumors, using radiation therapy. During radiation therapy, the targeted biological tissue is selectively exposed to therapeutic doses of radiation, preferably in a manner whereby the target tissue is killed, while sparing surrounding healthy tissue. Recently, it has been discovered that the use of hyperthermia (HT) therapy can be used as an adjunct to standard radiation therapy to increase the efficacy of the treatment. Hyperthermia can be defined as the treatment of disease by raising body temperature. Hyperthermia for the treatment of cancer involves the use of heating devices, such as microwave applicators, ultrasound, low energy radio frequency conduction probes, or a sophisticated thermometry system of micro-thermocouples placed externally, interstitially, or in the natural cavities of the body to make cancerous tumors more operable, radiosensitive, or susceptible to cancer therapy measures. Hyperthermia can be applied prior to, during, and/or subsequent to the radiation therapy.

According to a study published in the May 1, 2005 edition of the Journal of Clinical Oncology, patients with post-mastectomy chest wall recurrence of breast cancer who were given HT therapy experienced complete response (total disappearance of the tumor) at a rate nearly three times higher than those patients who received radiation treatment alone. The use of adjuvant hyperthermia also demonstrated a significant improvement in tumor control, among patients with recurrent melanoma as well as head and neck and other tumors when compared to stand-alone radiation therapy. It is thought that when combined with radiation therapy, hyperthermia creates a mechanism that interferes with the cellular repair of radiation-induced DNA damage.

During a radiation treatment session, the position and movement of the target tissue can be monitored by an imaging system, such as a fluoroscopic imaging device, magnetic resonant imaging (MRI) device, computed tomography (CT) device, or positron emission tomography (PET) device. The radiation beam can then be adjusted to ensure that the target tissue is in a desired position while the radiation is being delivered. Tracking of the target tissue can be accomplished using artificially placed internal markers as reference points. While generally successful, however, this tracking technique requires the additional step of placing the markers within the patient's body.

Thus, there remains a need to provide an improved system and method capable of applying radiation/HT therapy to a target tissue region, while tracking the position and/or movement of the target tissue region to facilitate focused treatment of the target tissue region.

SUMMARY OF THE INVENTION

In accordance with one aspect of the present inventions, a method of treating a target tissue region (e.g., malignant tissue) of a patient's body is provided. The method comprises introducing a hyperthermic probe into contact with the target tissue region. In one method, the hyperthermic probe is percutaneously introduced into contact with the target tissue region, although other forms of probe introduction are contemplated by the invention. The method further comprises exposing the target tissue region to a therapeutic x-ray radiation beam, and operating the probe to increase the temperature of the target tissue region, thereby facilitating a therapeutic effect of the radiation beam. In one method, the hyperthermic probe is a tissue ablation probe (e.g., a radiofrequency (RF) ablation probe), in which case, the probe can be operated to ablate the target tissue region. The hyperthermic probe may be operated to increase the temperature of the target tissue region prior to and/or while traversing the target tissue region with the radiation beam.

The method further comprises acquiring image data of the probe while in contact with the target tissue region, wherein the image data contains a fiducial datum, determining a position of the target tissue region within a treatment coordinate system (e.g., a three-dimensional coordinate system) based on the fiducial datum, and spatially adjusting the radiation beam relative to the target tissue region based on the determined position of the target tissue region. In one method, the radiation beam is spatially adjusted by adjusting a position and/or orientation of the radiotherapy device that generates the radiation beam relative to the target tissue region. The radiation beam may be spatially adjusted relative to the target tissue region by adjusting an absolute position and/or orientation of the radiation beam or by adjusting an absolute position and/or orientation of the target tissue region. In another method, the hyperthermic probe comprises an array of electrodes, in which case, the image data of the electrode array may contain the fiducial datum. In an optional method, the radiation beam is dynamically adjusted in response to movement of the target tissue region within the coordinate system.

In accordance with a second aspect of the present inventions, a tissue treatment system is provided. The system comprises a hyperthermic probe configured to be placed in contact with a target tissue region, and a source of thermal energy coupled to the hypothermic probe. The hyperthermic probe may be configured for being percutaneously introduced into contact with the target tissue region, although the hyperthermic probe may be configured to be introduced into contact with the target tissue region using other means. The hyperthermic probe may be a tissue ablation probe (e.g., a radiofrequency (RF) ablation probe), and the source of thermal energy may be a source of ablation energy (e.g., RF energy).

The tissue treatment system further comprises a radiotherapy device configured for exposing the target tissue region to an x-ray radiation beam. The radiotherapy device may include, e.g., a radiation source for emitting the radiation beam and an image acquisition module for receiving the radiation beam. The tissue treatment system further comprises an imaging device configured for generating image data of the hyperthermic probe while in contact with the target tissue region, wherein the image data contains a fiducial datum. If the radiotherapy device includes an image acquisition module, the imaging device that generates the image data may be image acquisition module. Alternatively, the imaging device may be independent from the radiotherapy device.

The tissue treatment system further comprises a positioning processor/controller configured for determining a position of the target tissue region within a treatment coordinate system (e.g., a three dimensional coordinate system) based on the fiducial datum, and spatially adjusting radiation beam relative to the target tissue region based on the determined position of the target tissue region. In one embodiment, the hyperthermic probe may have an array of electrodes, in which case, the image data of the electrode array may contain the fiducial datum. The positioning processor/controller may be configured for spatially adjusting the radiation beam by adjusting an absolute position and/or orientation of the radiation beam or by adjusting an absolute position and/or orientation of the target tissue region. In an optional embodiment, the position processor/controller may be configured for dynamically adjusting the radiation beam in response to movement of the target tissue region within the coordinate system.

Other and further aspects and features of the invention will be evident from reading the following detailed description of the preferred embodiments, which are intended to illustrate, not limit, the invention.

BRIEF DESCRIPTION OF DRAWINGS

The drawings illustrate the design and utility of preferred embodiment(s) of the invention, in which similar elements are referred to by common reference numerals. In order to better appreciate the advantages and objects of the invention, reference should be made to the accompanying drawings that illustrate the preferred embodiment(s). The drawings, however, depict the embodiment(s) of the invention, and should not be taken as limiting its scope. With this caveat, the embodiment(s) of the invention will be described and explained with additional specificity and detail through the use of the accompanying drawings in which.

DETAILED DESCRIPTION OF THE ILLUSTRATED EMBODIMENTS

Figure 1:
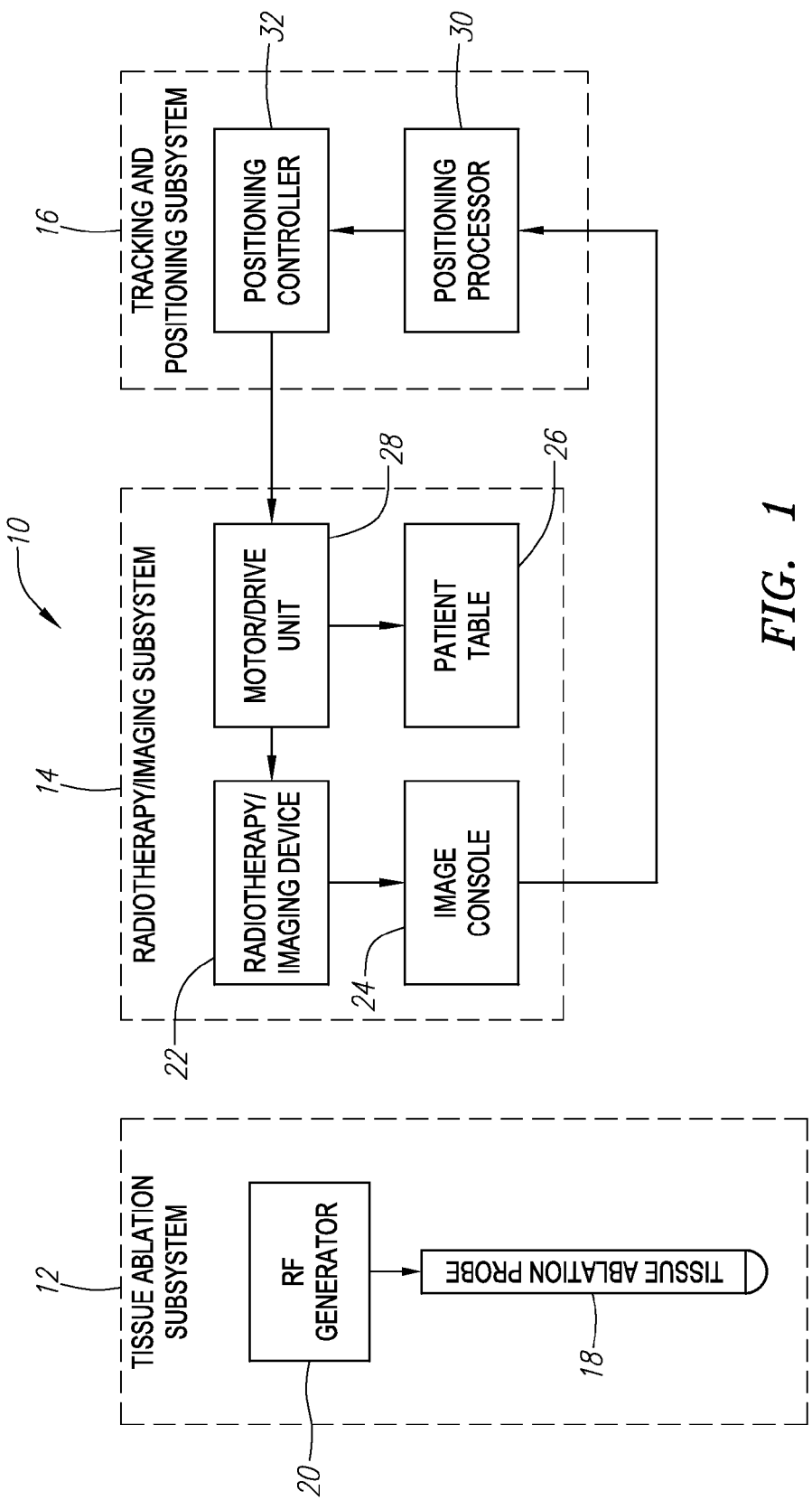
FIG. 1 is a block diagram of a tissue treatment system constructed in accordance with a preferred embodiment of the present invention.

Referring to FIG. 1, an exemplary tissue treatment system 10 constructed in accordance with the present inventions will be described. The tissue treatment system 10 is particularly suited for treating proliferative tissue of a patient, such as a malignant tumor, using a combination of x-ray radiation and hyperthermic therapy. The tissue treatment system 10 generally comprises (1) a tissue ablation subsystem 12 for therapeutically ablating the target tissue region; (2) a radiotherapy/imaging subsystem 14 for therapeutically exposing the target tissue region to an x-ray radiation beam and for acquiring diagnostic images of the target tissue region; and (3) a tracking and positioning subsystem 16 configured for tracking inadvertent movements of the target tissue region due to, e.g., the normal respiratory movement of the patient or the shifting of an organ containing the target tissue region, and automatically moving the patient relative to the radiation beam to ensure that the radiation beam is focused on the moving target tissue region.

As will be described in further detail below, the tissue ablation subsystem 12 is not only configured for therapeutically ablating the target tissue region, it is also capable of elevating the temperature of the tissue region, thereby increasing the therapeutic effect of the radiation therapy. It should be noted that the elements illustrated in FIG. 1 are functional in nature, and are not meant to limit the structure that performs these functions in any manner. For example, several of the functional blocks can be embodied in a single device, or one of the functional blocks can be embodied in multiple devices. Also, the functions can be performed in hardware, software, or firmware.

I. Ablation Subsystem

The tissue ablation subsystem 12 generally includes a tissue ablation probe 18 for introduction into the body of a patient for ablative treatment of the target tissue region, and a radio frequency (RF) generator 20 configured for generating and delivering RF power to the tissue ablation probe 18.

Figure 2:
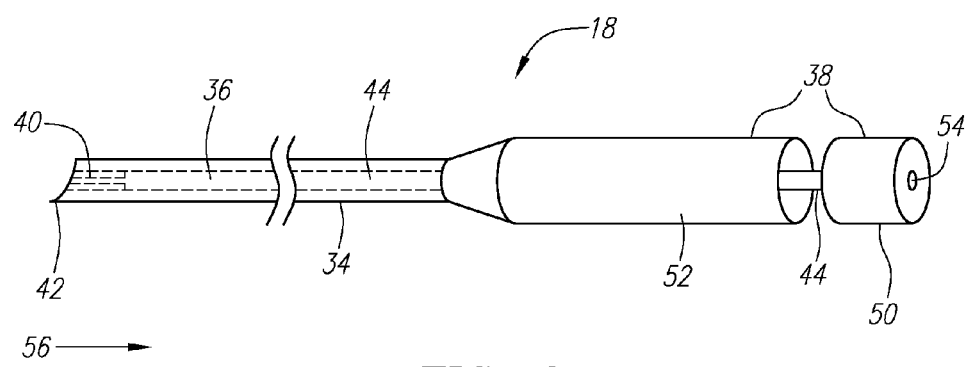
FIG. 2 is a perspective view of a tissue ablation probe used in the tissue treatment system of FIG. 1, wherein an array of electrodes is particularly shown retracted.
Figure 3:
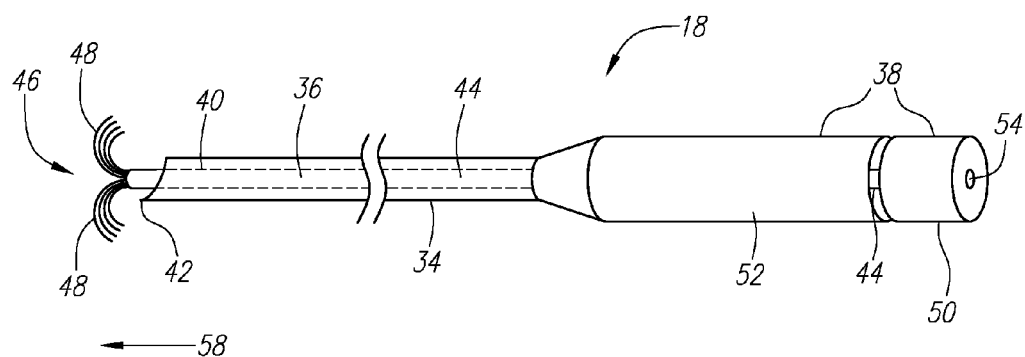
FIG. 3 is a perspective view of the tissue ablation probe of FIG. 2, wherein the array of electrode tines is particularly shown deployed.

Referring to FIGS. 2 and 3, the ablation probe 18 generally comprises an elongated cannula 34, an inner probe 36 slideably disposed within the cannula 34, and a handle assembly 38. As will be described in further detail below, the cannula 34 serves to deliver the active portion of the inner probe 36 to the target tissue. The cannula 34 has a suitable length, typically in the range of 5 cm to 30 cm, preferably from 10 cm to 20 cm. The cannula 34 has an outside diameter consistent with its intended use, typically being from 1 mm to 5 mm, usually from 1.3 mm to 4 mm. The cannula 34 has an inner diameter in the range of 0.7 mm to 4 mm, preferably from 1 mm to 3.5 mm.

The cannula 34 comprises a central lumen 40 through which the inner probe 36 is slidably disposed. The cannula 34 has sufficient columnar strength, such that it can penetrate and be advanced through tissue. The cannula 34 may optionally comprise a tissue penetrating tip 42 composed of a suitable material, such as plastic or metal. The tissue penetrating tip 42 has a sharp point that is created by beveling the distal end of the tissue penetrating tip 42. It is noted that the use of a sharp tissue penetrating tip 42 allows the cannula 34 to penetrate through skin and underlying fascia, thereby facilitating a percutaneous introduction procedure. The use of a sharp tissue penetrating tip 42 has other advantages as well. The sharp tissue penetrating tip 42 allows the cannula 34 to be introduced into tough tissue where tumors may be found. For example, in the case of hepatocellular carcinoma (HCC), the liver is very cirrhotic, with a tough, fibrous nature that requires a sharp tip for continued penetration to the tumor. The sharp tissue penetrating tip 42 also allows penetration of tumors that are unstable within the surround tissue. For example, breast tumors, in which there is an increasing interest for ablation, have been likened to a "golf ball in a gelatin." In this case, accurate targeting of a breast tumor by an ablation probe requires a quick, accurate stab with a sharp tip. Lung tumors have been described with similar properties.

The inner probe 36 comprises a reciprocating shaft 44 and an array 46 of tissue penetrating needle electrodes 48 extending from the distal end of the shaft 44. Like the cannula 34, the inner probe shaft 44 is rigid and is composed of a suitable material, such as plastic or metal. Alternatively, the inner probe shaft 44 can be composed of a semi-rigid material, such as, e.g., stainless steel braid, that when radially constrained by the inner surface of the cannula 34, provides the necessary columnar strength for the inner probe 36 to be distally pushed within the lumen 40 of the cannula 34. To facilitate coaxial movement between the inner probe shaft 44 and the cannula 34, the inner surface of the cannula 34 and/or the outer surface of the inner probe shaft 44 can be coated with a lubricious material. The electrode array 46 can be mounted anywhere on the inner probe shaft 44. However, the electrodes 48 will typically be fastened to the distal end of the inner probe shaft 44, though the proximal ends of the individual electrodes 48 can extend up to, or beyond, the proximal end of the shaft 44.

Each of the needle electrodes 48 is a small diameter metal element, which can penetrate into tissue as it is advanced into a target site within the target region. For example, each electrode 48 can be composed of a single wire that is formed from resilient conductive metals having a suitable shape memory. Many different metals such as stainless steel, nickel-titanium alloys, nickel-chromium alloys, and spring steel alloys can be used for this purpose. If composed of a non-radiopaque substance, such as nickel-titanium alloy, a coating comprising gold or gold alloy, tantalum or other radiopaque materials can be applied over the electrodes 48. The wires may have circular or non-circular cross-sections, but preferably have rectilinear cross-sections. When constructed in this fashion, the needle electrodes 48 are generally stiffer in the transverse direction and more flexible in the radial direction. The circumferential alignment of the needle electrodes 48 within the cannula 34 can be enhanced by increasing transverse stiffness. Exemplary needle electrodes will have a width in the circumferential direction in the range of 0.2 mm to 0.6 mm, preferably from 0.35 mm to 0.40 mm, and a thickness, in the radial direction, in the range of 0.05 mm to 0.3 mm, preferably from 0.1 mm to 0.2 mm.

The distal ends of the needle electrodes 48 may be honed or sharpened to facilitate their ability to penetrate tissue. The distal ends of these needle electrodes 48 may be hardened using conventional heat treatment or other metallurgical processes. The needle electrodes 48 may be partially covered with insulation, although they will be at least partially free from insulation over their distal ends. The proximal ends of the needle electrodes 48 may be directly coupled to the proximal end of the inner probe shaft 44, or alternatively, may be indirectly coupled thereto via other intermediate conductors, such as RF wires (not shown). Optionally, the inner probe shaft 44 and any component between the shaft 44 and the needle electrodes 48 are composed of an electrically conductive material, such as stainless steel, and may therefore conveniently serve as intermediate electrical conductors.

The handle assembly 38 includes a handle member 50 mounted to the proximal end of the inner probe shaft 44, and a handle sleeve 52 mounted to the proximal end of the cannula 34. The handle member 50 is slidably engaged with the handle sleeve 52 (and the cannula 34). The handle member 50 and handle sleeve 52 can be composed of any suitable rigid material, such as, e.g., metal, plastic, or the like. The handle assembly 38 also includes an electrical connector 54 mounted within the handle member 50. The electrical connector 54 is electrically coupled to the electrode array 46, e.g., via the inner probe shaft 44 (which will be electrically conductive) or separate wires (not shown). The electrical connector 54 is configured for mating with the proximal end of a RF cable (not shown). Alternatively, the RF cable may be hardwired within the handle member 50.

As illustrated in FIG. 2, the inner probe shaft 44 may be longitudinally translated in the proximal direction 56 relative to the cannula 34 by holding the handle sleeve 52 and displacing the handle member 50 in the proximal direction 56, thereby retracting the electrode array 46 into the distal end of the cannula 34. When retracted within the cannula 34, the electrode array 46 is placed in a radially collapsed configuration, and each needle electrode 48 is constrained and held in a generally axially aligned position within the cannula 34 to facilitate its introduction into the target tissue region.

As illustrated in FIG. 3, the inner probe shaft 44 may be longitudinally translated in the distal direction 58 relative to the cannula 34 by holding the handle sleeve 52 and displacing the handle member 50 in the distal direction 58, thereby deploying the electrode array 46 out of the distal end of the cannula 34. When deployed from the cannula 34, the electrode array 46 is placed in a three-dimensional configuration that usually defines a generally spherical or ellipsoidal volume having a periphery with a maximum radius in the range of 0.5 cm to 5 cm. The needle electrodes 48 are resilient and pre-shaped to assume a desired configuration when advanced into tissue. In the illustrated embodiment, the needle electrodes 48 diverge radially outwardly from the cannula 34 in a uniform pattern, i.e., with the spacing between adjacent needle electrodes 48 diverging in a substantially uniform pattern or symmetric pattern or both. In the illustrated embodiment, the needle electrodes 48 evert proximally, so that they face partially or fully in the proximal direction when fully deployed. In exemplary embodiments, pairs of adjacent needle electrodes 48 can be spaced from each other in similar or identical, repeated patterns that can be symmetrically positioned about an axis of the inner probe shaft 44.

It will be appreciated by one of ordinary skill in the art that a wide variety of patterns can be used to uniformly cover the region to be treated. It should be noted that a total of eight needle electrodes 48 are illustrated in FIG. 3. Additional needle electrodes can be added in the spaces between the illustrated electrodes 48, with the maximum number of needle electrodes 48 determined by the electrode width and total circumferential distance available. Thus, the needle electrodes 48 could be quite tightly packed.

In the illustrated embodiment, the RF current is delivered to the electrode array 46 in a monopolar fashion, which means that current will pass from the electrode array 46, which is configured to concentrate the energy flux in order to have an injurious effect on the surrounding tissue, and a dispersive electrode (not shown), which is located remotely from the electrode array 46 and has a sufficiently large area (typically 130 $cm^2$ for an adult), so that the current density is low and non-injurious to surrounding tissue. In the illustrated embodiment, the dispersive electrode may be attached externally to the patient, e.g., using a contact pad placed on the patient's flank.

Further details regarding electrode array-type probe arrangements are disclosed in U.S. Pat. No. 6,379,353, which is hereby expressly incorporated by reference.

Referring back to FIG. 1, the RF generator 20 may be a conventional general purpose electrosurgical power supply operating at a frequency in the range from 300 kHz to 9.5 MHz, with a conventional sinusoidal or non-sinusoidal wave form. Such power supplies are available from many commercial suppliers, such as Valleylab, Aspen, Bovie, and Ellman. Most general purpose electrosurgical power supplies, however, are constant current, variable voltage devices and operate at higher voltages and powers than would normally be necessary or suitable. Thus, such power supplies will usually be operated initially at the lower ends of their voltage and power capabilities, with voltage then being increased as necessary to maintain current flow. More suitable power supplies will be capable of supplying an ablation current at a relatively low fixed voltage, typically below 200 V (peak-to-peak). Such low voltage operation permits use of a power supply that will significantly and passively reduce output in response to impedance changes in the target tissue. The output will usually be from 5 W to 300 W, usually having a sinusoidal wave form, but other wave forms would also be acceptable. Power supplies capable of operating within these ranges are available from commercial vendors, such as Boston Scientific Therapeutics Corporation. Preferred power supplies are models RF-2000 and RF-3000, available from Boston Scientific Corporation.

II. Radiation/Imaging Subsystem

Figure 4:
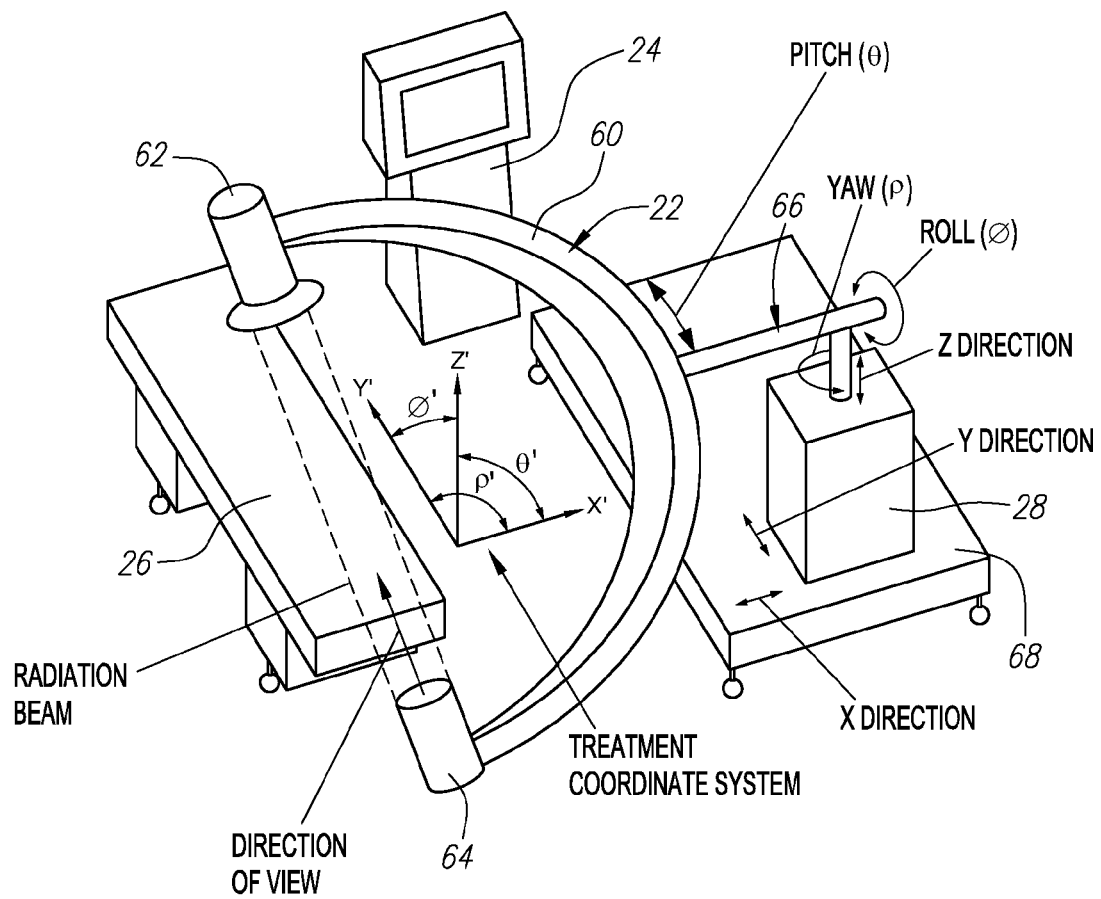
FIG. 4 is a perspective view of a radiotherapy/imaging subsystem used in the tissue ablation system of FIG. 1.

Referring to FIGS. 1 and 4, the radiotherapy/imaging subsystem 14 comprises a radiotherapy/imaging device 22 for emitting an x-ray radiation beam that intersects the target tissue region of the patient, an image console 24 for controlling and acquiring image information from the radiotherapy/imaging device 22 and displaying the information to medical personnel as a two-dimensional image, and a table 26 on which the patient is placed during the radiotherapy process. It can be appreciated that although these elements are illustrated as being mechanically separate from each other, any combination of these elements can be integrated with each other.

The radiotherapy/imaging device 22 comprises a gantry, and in particular a C-arm 60, a therapeutic x-ray source 62 mounted to one end of the C-arm 60, and an image acquisition module 64 mounted to the other end of the C-arm 60 opposite the x-ray source 62. The table 26 is configured for positioning the target tissue region between the ends of the C-arm 60, and thus, between the therapeutic x-ray source 62 and the image acquisition module 64. Thus, the therapeutic x-ray source 62 emits an x-ray radiation beam, which transits the target tissue region of the patient, thereby therapeutically necrosing the target tissue region. To confirm that the target tissue region of the patient has been accurately exposed to the radiation beam, the image acquisition module 64, in a standard manner, converts the tissue modulated x-ray radiation into electrical signals, which are representative of low-contrast two-dimensional images of the tissue, and stored as image data. As will be described in further detail below, the image data contains a fiducial datum used by the positioning subsystem 16 to track the location of the treatment region. A secondary diagnostic radiation source and imaging module (not shown) may be optionally provided to supply high-contrast two-dimensional or three-dimensional images of the target tissue region. These optional devices can be mounted on the C-arm or on an independent mounting device. Radiotherapy/imaging devices that provide an additional diagnostic source and imager are described in U.S. Pat. No. 6,888,919, which is expressly incorporated herein by reference.

The radiotherapy/imaging device 22 further comprises a motor/drive unit 28 on which the C-arm 60 is supported via a pivot assembly 66, and a base 68 on which the motor/drive unit 28 is mounted. The motor/drive unit 28 is configured for actuating movement of the C-arm 60, within a therapeutic coordinate system (x, y, z, $\theta$, $\phi$, $\rho$). In particular, the motor/drive unit 28 can actuate the pivot assembly 66 to pivot the C-arm 60 about three orthogonal axes (pitch ($\theta$), roll ($\phi$), and yaw ($\rho$)) to allow radiation of the patient from several different angles. Typical views include anterior-posterior (0° pitch, 0°/180° roll), lateral (90°/−90° pitch, 0° roll), and anterior oblique (45°/−45° pitch, 0° roll). In addition, the motor/drive unit 28 is configured to rectilinearly translate the C-arm 60 in three-dimensional space (e.g., in x-, y-, and z-directions), so that, given a set angular orientation of the C-arm 60, the target tissue region can be located within the radiation beam. In the illustrated embodiment, the motor/drive unit 66 is coupled to the base 68 via a translational assembly (not shown). In this manner, the motor/drive unit 28 can move relative to the base 68 to effect rectilinear translation of the C-arm 60 in the x- and y-directions. The motor/drive unit 28 can move the pivot assembly 66 up and down to effect rectilinear translation of the C-arm 60 in the z-direction. Alternatively, the patient table 26, instead of, or in addition to, the C-arm 60, can be configured to be rectilinearly translated.

As will be described in further detail below, the motor/drive unit 28 may be automatically controlled by the positioning subsystem 16 in order to adjust the location of the radiation beam as the target tissue region moves. Alternatively, the motor/drive unit 28 is controlled only to initially adjust the location of the radiation beam relative to the target tissue region. A secondary motor/drive unit (not shown) may be integrated with the radiation source 62, so that movement of the radiation beam may be more responsive to movements of the target tissue region. In this case, the relatively large C-arm 60 remains stationary, while the radiation source 62 moves relative to the C-arm 60 to steer the radiation beam. Alternatively, the radiation beam may be electronically steered, e.g., using a phased array, so that no components need be physically moved, thereby increasing the responsiveness of the radiation mean to the moving target tissue region.

III. Tracking and Positioning Subsystem

Referring back to FIG. 1, the tracking the target tissue region of the patient and positioning subsystem 16 is configured for adjusting the therapeutic radiation beam relative to the patient, so that only the target tissue region is being radiated at any given time. To this end, the tracking and positioning subsystem 16 comprises a position processor 30 for continuously determining the desired position and orientation of the radiation beam generated by the radiotherapy/imaging device 60 that will place the target tissue region of the patient within the radiation beam (which presumably will change as the position of the target tissue region changes), and a position controller 32 for placing the radiation beam within the desired position and orientation. As briefly discussed above, the position and orientation of the C-arm 60 will be changed to effect a change in the position and orientation of the radiation beam, although alternatively, the position and orientation of the radiation beam may be changed using other means, e.g., by altering the position and orientation of the radiation source 62 relative to the C-arm 60 or by electronically steering the radiation beam. It should be noted that although the position processor 30 and position controller 32 are illustrated as being separate from the radiotherapy/imaging subsystem 14, these components can be conveniently incorporated into the image console 24.

Significant to the present invention, the image processor 30 determines the desired position and orientation of the radiation beam by using the tissue ablation probe 18, and in particular, the needle electrodes 48, as fiducial elements. In particular, the image processor 30 obtains from the radiotherapy/imaging subsystem 14 image data of the tissue ablation probe 18 while located within the target tissue region, and analyzes the representations of the electrodes 48 within the image, which are used as a fiducial datum to determine the position of the tissue treatment region within the treatment coordinate system. Notably, the intersection of the electrodes 48 provides a "boresight" that will presumably be located within the tissue target region, thereby providing an efficient and effective means for determining the position of the target tissue region. Based on this determined position of the tissue treatment region, the desired position and orientation of the radiation beam can then be determined, so that the isocenter of the radiation beam intersects the tissue treatment region.

Processing of the image data to determine the position of the target tissue region within the treatment coordinate system can be accomplished using standard image processing techniques. Notably, the three-dimensionality of the electrode array 46 allows the position of the target tissue region to be determined using a single image, although several images from different perspectives can be acquired to increase the accuracy of such determination.

Figure 5:
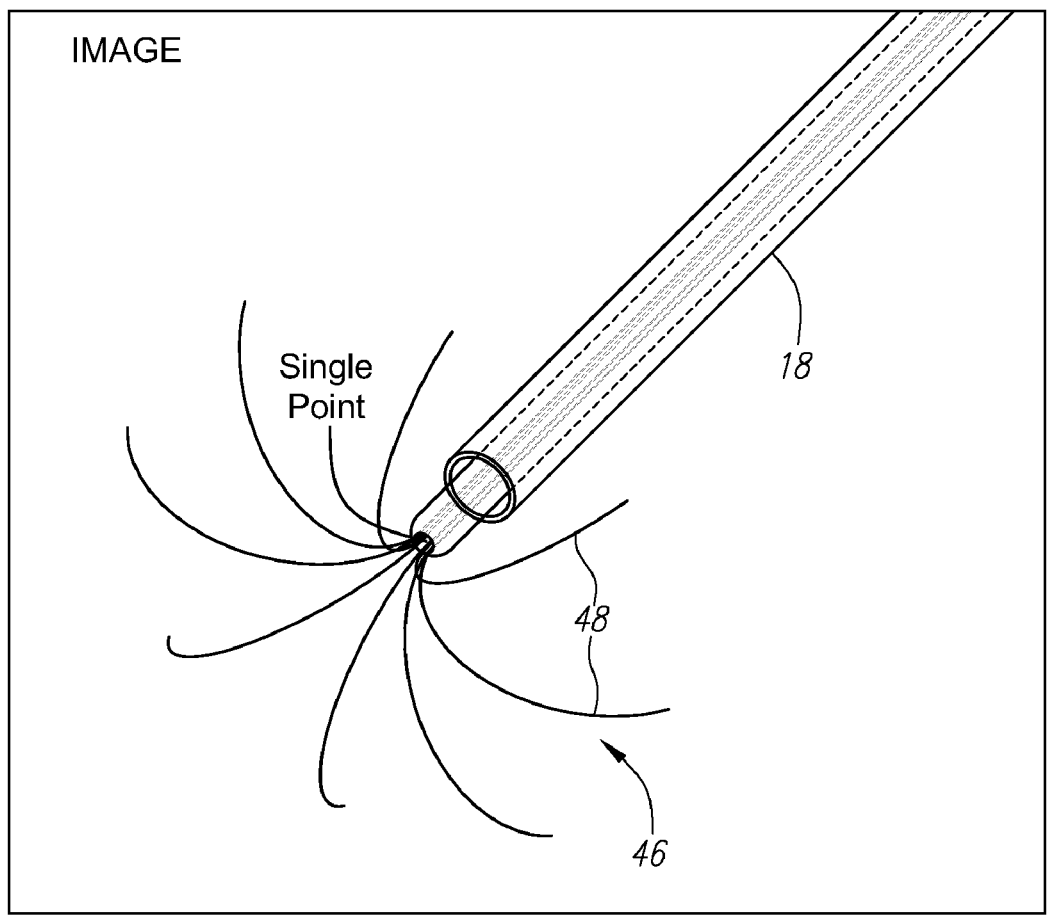
FIG. 5 is a view of an image of the tissue ablation probe of FIG. 3.

For example, FIG. 5 illustrates an exemplary image of the electrode array 46. As can be seen, the electrodes 48 converge to a single trackable point, and the electrode array 46 is oriented at an angle relative to the direction of view (coming straight out of the figure) of the imaging device that has acquired the image. This angle, as well as the distance between the electrode array 46 (in particular, the single point at which the electrodes 48 converge) and the imaging device, can be determined using a standard image processing technique. Because the position and orientation of the image device is known within the treatment coordinate system, the position of the electrode array 46, and thus the target tissue region, can be determined within the treatment coordinate system.

In the illustrated embodiment, the imaging device is the image acquisition module 64 illustrated in FIG. 4, in which case, the position and orientation of the image device within the treatment coordinate system can be easily obtained due to the close mechanical correlation between the image acquisition module 64 and the therapeutic radiation source 62. However, an image acquired from any image device whose position and orientation can be determined relative to the radiation source 62 can be processed to determine the position of the electrode array 46, and thus, the tissue treatment region, within the treatment coordinate system.

IV. Method of Use

Having described the structure of the tissue treatment system 10, its operation in treating a target tissue region will now be described. The target tissue region may be located anywhere in the body where radiation/hyperthermic exposure may be beneficial. Most commonly, the tissue region will be located within an organ of the body, such as the liver, kidney, pancreas, breast, prostrate (not accessed via the urethra), and the like. The volume of the tissue region will typically be in the range of 1 $cm^3$ to 150 $cm^3$, and often from 2 $cm^3$ to 50 $cm^3$.

The target tissue region may be identified using conventional imaging techniques capable of elucidating a target tissue, e.g., tumor tissue, such as ultrasonic scanning, magnetic resonance imaging (MRI), computer-assisted tomography (CAT), fluoroscopy, nuclear scanning (using radiolabeled tumor-specific probes), and the like. Preferred is the use of high resolution ultrasound of the tumor or other lesion being treated, either intraoperatively or externally.

Figure 6A:
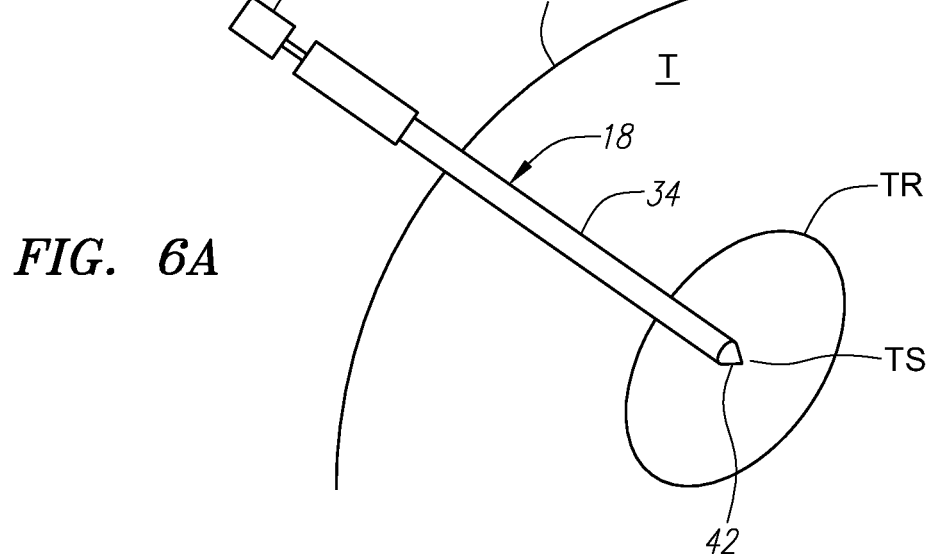
FIGS. 6A-6E are side views illustrating a method of treating tissue using the tissue treatment system of FIG. 1.

Referring now to FIGS. 6A-6E, the operation of the tissue treatment system 10 is described in treating a target tissue region TR beneath the skin or an organ surface S of a patient. Although a single tissue region TR is illustrated for purposes of brevity, the tissue treatment system 10 may alternatively be used to treat multiple treatment regions TR. With the patient preferably lying on the table 26, the tissue ablation probe 18 is first introduced through the tissue T, so that the distal tip 42 of the cannula 34 is located at a target site TS within the tissue region TR (FIG. 6A).

This can be accomplished using any one of a variety of techniques. In the preferred method, the ablation probe 18 is percutaneously introduced to the tissue region TR directly through the patient's skin or through an open surgical incision. In this case, the distal tip 42 of the cannula 34 may be sharpened to facilitates introduction of the ablation probe 18 to the tissue region TR. In such cases, it is desirable that the cannula 34 be sufficiently rigid, i.e., have a sufficient column strength, so that it can be accurately advanced through tissue T. In other cases, the cannula 34 may be introduced using an internal stylet that is subsequently exchanged for the inner probe 36. In this latter case, the inner probe shaft 44 can be relatively flexible, since the initial column strength will be provided by the stylet. More alternatively, a component or element may be provided for introducing the cannula 34 to the target ablation site TS. For example, a conventional sheath and sharpened obturator (stylet) assembly can be used to initially access the tissue T. The assembly can be positioned under ultrasonic or other conventional imaging, with the obturator/stylet then removed to leave an access lumen through the sheath. The cannula 34 can then be introduced through the sheath lumen, so that the distal end of the cannula 34 advances from the sheath into the target ablation site TS.

Figure 6B:
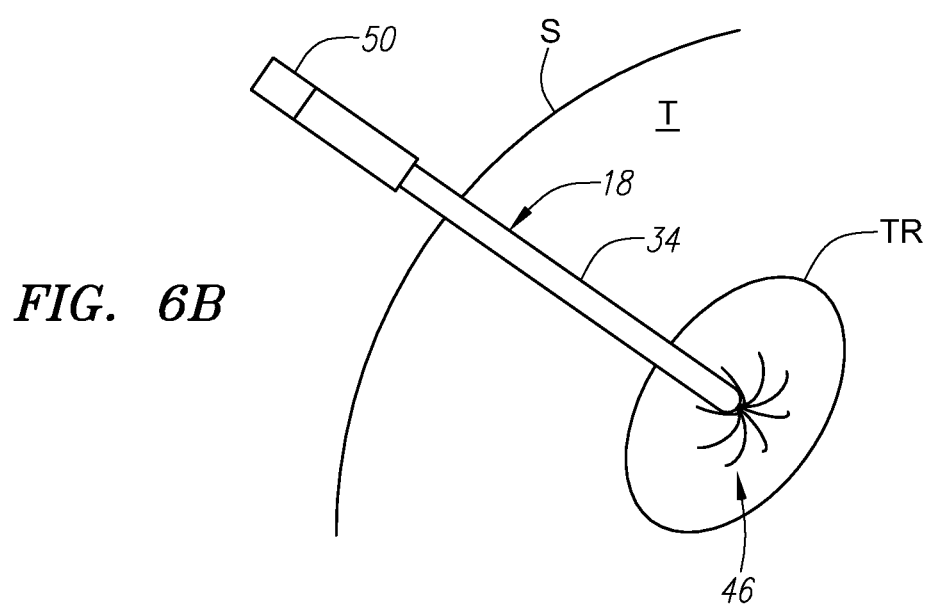
Figure 6C:
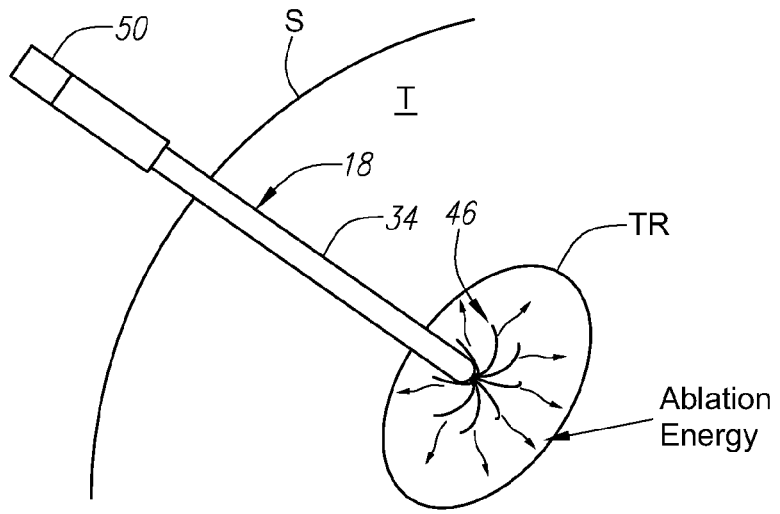

Once the ablation probe 18 is properly positioned, the handle member 50 of the ablation probe 18 is distally advanced to deploy the electrode array 46 radially outward from the distal end of the cannula 34 until the electrode array 46 fully everts within the respective target ablation site TS (FIG. 6B). The RF generator 20 (shown in FIG. 1) is connected to the ablation probe 18 and operated, thereby conveying RF ablation energy to the electrode array 46 and ablating the tissue region TR (FIG. 6C). In addition to necrosing the tissue region TR, the temperature of the tissue region TR becomes elevated, thereby preconditioning the tissue region TR for subsequent radiation treatment, as discussed below.

Figure 6D:
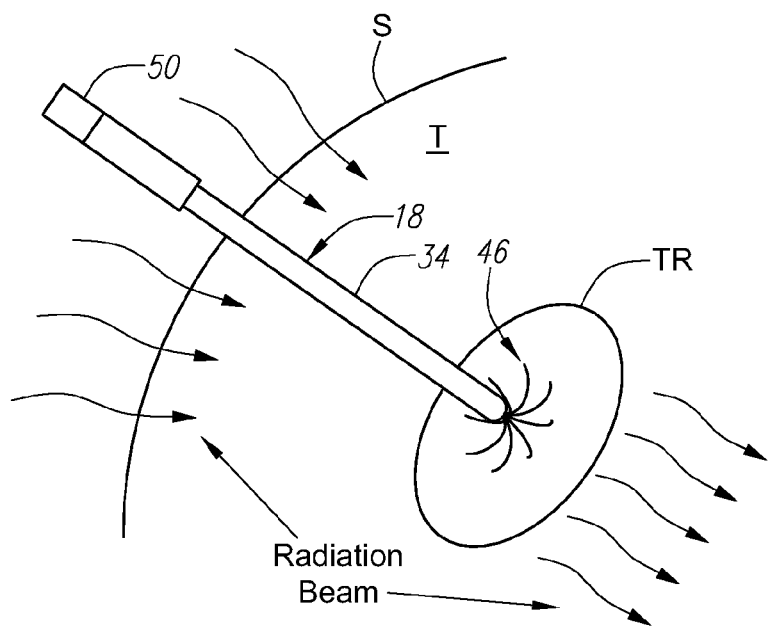

Next, the table 26 is positioned relative to the C-arm 60, so that the treatment region TR lies between the radiation source 62 and the image acquisition module 64. The C-arm 60 is then moved, so that the isocenter of the radiation beam that will be generated by the radiation source 62 intersects the tissue region TR, and then the radiotherapy/imaging subsystem 14 is operated, so that the radiation beam traverses the tissue region TR, thereby further necrosing the deeper tissue not otherwise necrosed by the initial RF ablation (FIG. 6D). Notably, the elevated temperature of the tissue region TR resulting from the initial RF ablation facilitates the therapeutic effect of the radiation therapy, as previously discussed. Optionally, the RF generator may be operated during the radiation therapy, such that the tissue region TR is heated, thereby maintaining the elevated temperature of the tissue region TR.

Figure 6E:
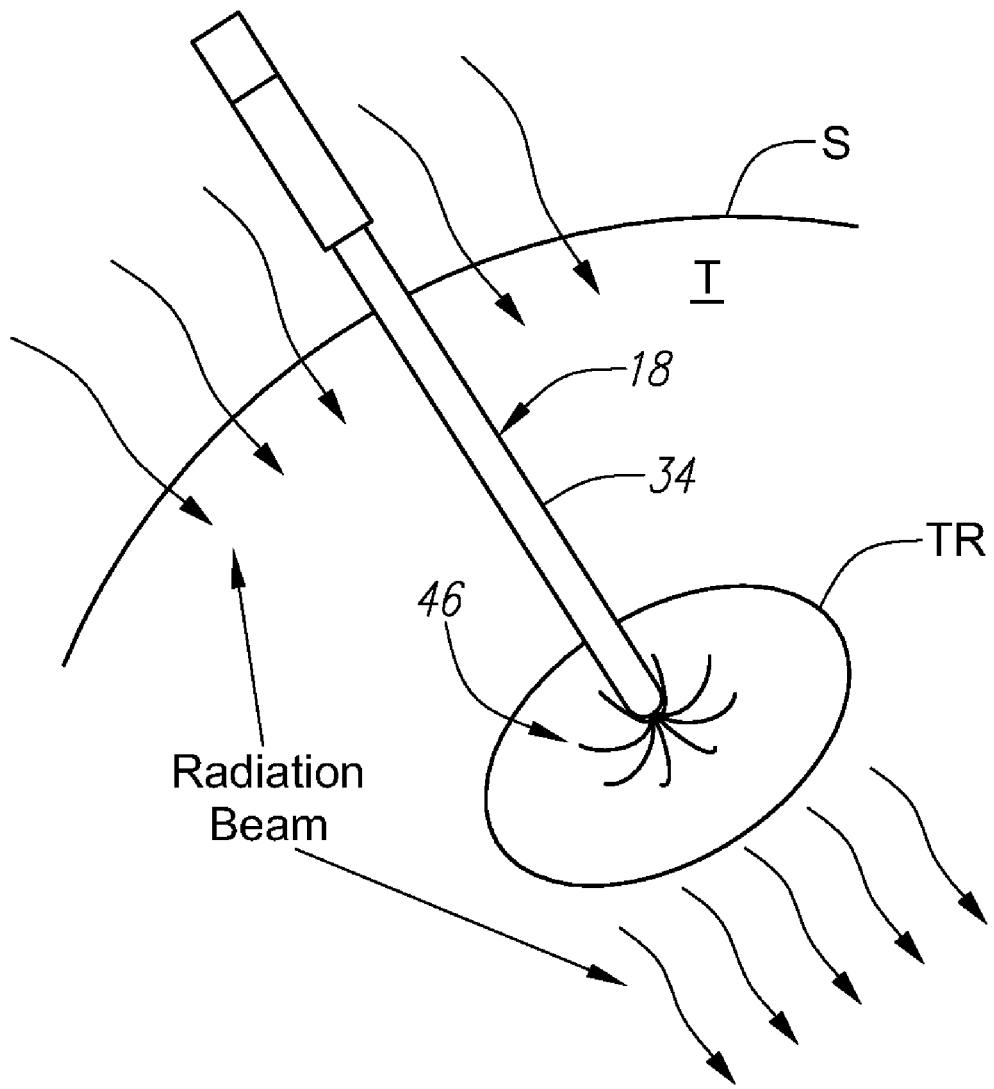

The image acquisition module 64 captures the radiation that traverses the tissue region TR, thereby causing the tissue region TR, along with the electrode array 46, to be displayed on the image console 24. Alternatively, a separate image acquisition module captures radiation traversing the treatment region TR from a separate diagnostic radiation source (both not shown), which is displayed on the image console 24. The positioning processor 30 processes the image data, determines the position of the electrode array 36, and thus the tissue region TR, within the treatment coordinate system, based on the electrode representations (i.e., the fiducial datum) within the image data, and determines the desired position and orientation of the radiation beam based on the determined position of the tissue region TR. The positioning controller 32 then adjusts the position and orientation of the radiation beam to match its desired position and orientation by, e.g., moving the C-arm 60 relative to the patient table 26, or alternatively, moving the radiation source 62 relative to the C-arm 60 and/or electronically steering the radiation beam. Thus, as the tissue region TR moves, e.g., due to respiration of the patient, the radiation beam will be adjusted so that its isocenter intersects the tissue region TR (FIG. 6E).

Although particular embodiments of the present invention have been shown and described, it will be understood that it is not intended to limit the present invention to the preferred embodiments, and it will be obvious to those skilled in the art that various changes and modifications may be made without departing from the spirit and scope of the present invention. Thus, the present inventions are intended to cover alternatives, modifications, and equivalents, which may be included within the spirit and scope of the present invention as defined by the claims.

What is claimed is:

1. A tissue treatment system, comprising:
    a tissue ablation subsystem comprising a hyperthermic probe configured to be placed in contact with a target tissue region and an radio frequency generator operatively coupled to the ablation probe, the probe comprising a plurality of electrodes configured to converge in a single location comprising a fiducial datum;
    a radiotherapy/imaging subsystem comprising a radiotherapy device configured for exposing the target tissue region to an x-ray radiation beam and an image console configured to acquire and display image data as a two-dimensional image, the image data containing the fiducial datum; and
    a tracking and positioning subsystem configured for tracking inadvertent movements of the target tissue region within a treatment coordinate system based on the fiducial datum, the tracking and positioning subsystem configured to spatially adjust the radiation beam relative to the target tissue region based on the determined position of the target tissue region.

2. The tissue treatment system of claim 1, wherein the hyperthermic probe comprises an elongated cannula and an inner probe slideably disposed within the cannula, the plurality of electrodes disposed at a distal end of the inner probe.

3. The tissue treatment system of claim 1, the radiotherapy/imaging subsystem comprising a moveable gantry configured to move relative to a table.

4. The tissue treatment system of claim 3, wherein the gantry comprises a C-arm with an x-ray source mounted at one of the C-arm and an image acquisition device mounted to the other end of the C-arm.

5. The tissue treatment system of claim 4, further comprising a motor/drive unit configured to move the x-ray source relative to the target tissue region.

6. The tissue treatment system of claim 3, further comprising a motor/drive unit supporting the C-arm.

7. The tissue treatment system of claim 6, wherein the tracking and positioning subsystem is operatively connected to the motor/drive unit.

8. The tissue treatment system of claim 3, wherein the table is configured for rectilinear translation.

9. The tissue treatment system of claim 1, wherein the tracking and positioning subsystem comprises a positioning processor and a controller configured for spatially adjusting the radiation beam by adjusting at least one of an absolute position and orientation of the radiation beam.

10. The tissue treatment system of claim 9, wherein the positioning processor and controller are incorporated into the image console.

11. The tissue treatment system of claim 1, wherein the x-ray radiation beam comprises a phased array.

12. The tissue treatment system of claim 1, wherein the plurality of electrodes comprise an array.

13. A method of treating a target tissue region of a subject's body, comprising:
    locating a subject on a table at least partially surrounded by a gantry having a radiation source and an imaging device;
    adjusting the gantry to place an isocenter of the radiation beam to intersect with the target tissue and exposing the target tissue region to a therapeutic x-ray radiation beam;
    introducing and operating a radio frequency probe into contact with the target tissue region, the radio frequency probe comprising a plurality of electrodes configured to converge in a single location comprising a fiducial datum;
    acquiring image data with the imaging device of the plurality of electrodes while in contact with the target tissue region, the image data containing the fiducial datum;
    determining a position of the target tissue region within a treatment coordinate system based on the fiducial datum; and
    spatially adjusting the radiation beam relative to the target tissue region based on the determined position of the target tissue region.

14. The method of claim 13, wherein the radiation beam is adjusted by moving one or more of the table and gantry.

15. The method of claim 13, wherein the radiation beam is electrically adjusted.

16. The method of claim 13, wherein image date is acquired continuously.

17. The method of claim 13, further comprising displaying a position of the tissue region and the plurality of electrodes on an image console.

18. The method of claim 13, wherein the radio frequency probe operates on the tissue region at the same time the radiation beam intersects the tissue region.

19. The method of claim 13, wherein the radio frequency probe is introduced into the body of the subject in a percutaneous manner.

20. A tissue treatment system, comprising:
    a table at least partially surrounded by a gantry having a radiation source and an imaging device;
    a hyperthermic probe configured to be placed in contact with a target tissue region and an radio frequency generator operatively coupled to the ablation probe, the probe comprising an array of electrodes configured to converge in a single location comprising a fiducial datum;
    a tracking and positioning subsystem configured for tracking movements of the target tissue region based on the fiducial datum, the tracking and positioning subsystem configured to spatially adjust a radiation beam from the radiation source relative to the target tissue region based on the determined position of the fiducial datum.

* * * * *